US 11,484,108 B2

(12) United States Patent
Song (10) Patent No.: US 11,484,108 B2
(45) Date of Patent: Nov. 1, 2022

(54) CARE INSTRUMENT (71) Applicant: Puzhen Life Co., Limited, Shatin (HK)

(72) Inventor: Baojie Song, New York, NY (US)

(73) Assignee: PUZHEN LIFE CO., LIMITED, Shatin (HK)

(*) Notice: Subject to any disclaimer, the term of this patent is extended or adjusted under 35 U.S.C. 154(b) by 559 days.

(21) Appl. No.: 16/534,068

(22) Filed: Aug. 7, 2019

(65) Prior Publication Data
US 2020/0260834 A1 Aug. 20, 2020

(51) Int. Cl.
*A45D 34/04* (2006.01)
*A45D 40/26* (2006.01)
(Continued)

(52) U.S. Cl.
CPC ............ *A45D 34/04* (2013.01); *A45D 40/26* (2013.01); *A61H 1/00* (2013.01); *A61H 23/02* (2013.01);
(Continued)

(58) Field of Classification Search
CPC .. A45D 34/04; A45D 40/26; A45D 2200/207; A45D 2034/005; A45D 2200/054; A45D 2200/155; A45D 34/00; A45D 2200/20; A45D 2200/15; A61H 23/02; A61H 1/00; A61H 2201/105;
(Continued)

(56) References Cited

U.S. PATENT DOCUMENTS 4,124,316 A * 11/1978 O'Rourke .......... A46B 11/0041
401/184
6,911,010 B2 * 6/2005 Dirks ..................... A61H 23/02
601/72
(Continued)

FOREIGN PATENT DOCUMENTS

CN 104771301 A 7/2015
CN 204582291 U 8/2015
(Continued)

OTHER PUBLICATIONS

U.S. Appl. No. 16/534,136, filed Aug. 7, 2019, Andy Lee.
(Continued)

*Primary Examiner* — David J Walczak
(74) *Attorney, Agent, or Firm* — Dorsey & Whitney LLP (57) ABSTRACT

A care instrument arranges a storage container and a peristaltic pump, with the storage container accommodating the care product, the peristaltic pump being configured to draw the care product from the storage container and deliver the care product to a surface of a housing. In this way, a user can apply care products while using the care instrument. By controlling the peristaltic pump by the control component, the care product is delivered to the surface of the housing in a timed and quantitative manner for precise and accurate delivery of the care product. The massaging component and the peristaltic pump can operate independently. When only the massaging component works independently, the care instrument functions in massaging, and when the massaging
(Continued)

component and the peristaltic pump work together, the care product delivered to the surface of the housing may be further uniformly dispersed by the massaging component.

20 Claims, 6 Drawing Sheets

(51) Int. Cl.
*A45D 34/00* (2006.01)
*A61H 23/02* (2006.01)
*A61H 1/00* (2006.01)
*A61H 7/00* (2006.01)
*A61M 21/02* (2006.01)
*A61M 21/00* (2006.01)
*F04B 43/12* (2006.01)

(52) U.S. Cl.
CPC .............. *A61M 21/02* (2013.01); *F04B 43/12* (2013.01); *A45D 2034/005* (2013.01); *A45D 2200/054* (2013.01); *A45D 2200/155* (2013.01); *A45D 2200/207* (2013.01); *A61H 7/005* (2013.01); *A61H 2201/0285* (2013.01); *A61H 2201/102* (2013.01); *A61H 2201/105* (2013.01); *A61H 2205/022* (2013.01); *A61M 2021/0016* (2013.01)

(58) Field of Classification Search
CPC .............. A61H 2201/102; A61H 7/005; A61H 2205/022; A61H 2201/0285; A61M 21/02; A61M 2021/0016; F04B 43/12
USPC ...................... 401/188 R, 261, 263, 265, 266
See application file for complete search history.

(56) References Cited

U.S. PATENT DOCUMENTS

| | | | | |
|---|---|---|---|---|
| 9,802,805 | B2* | 10/2017 | Singh | ................... B67D 1/0462 |
| 2008/0095645 | A1* | 4/2008 | Tam | ........................ B08B 3/026 |
| | | | | 417/477.1 |
| 2011/0264035 | A1* | 10/2011 | Yodfat | .............. A61M 5/14228 |
| | | | | 340/870.02 |
| 2012/0067977 | A1 | 3/2012 | Speigel | |
| 2014/0330289 | A1 | 6/2014 | Revivo | |

FOREIGN PATENT DOCUMENTS

| | | |
|---|---|---|
| CN | 204601078 U | 9/2015 |
| CN | 204601978 U | 9/2015 |
| CN | 105443363 | 3/2016 |
| CN | 105600140 A | 5/2016 |
| CN | 207308159 U | 5/2018 |
| CN | 108290028 | 7/2018 |
| CN | 207898646 U | 9/2018 |
| CN | 108968748 A | 12/2018 |
| CN | 109259413 | 1/2019 |
| CN | 208405744 U | 1/2019 |
| CN | 109963611 A | 7/2019 |
| KR | 20150010075 A | 1/2015 |
| WO | WO 199842401 | 10/1998 |

OTHER PUBLICATIONS

U.S. Appl. No. 16/534,162, filed Aug. 7, 2019, Andy Lee.
U.S. Appl. No. 16/534,136, filed Aug. 7, 2019, Lee.
U.S. Appl. No. 16/534,162, filed Aug. 7, 2019, Lee.

* cited by examiner

CARE INSTRUMENT

CROSS-REFERENCE TO RELATED APPLICATIONS

This application is a continuation-in-part of International Patent Application No. PCT/CN2019/077820, filed on Mar. 12, 2019, a continuation-in-part of International Patent Application No. PCT/CN2019/075067, filed on Feb. 14, 2019, and a continuation-in-part of International Patent Application No. PCT/CN2019/075066, filed on Feb. 14, 2019. In addition, this application claims priority to Chinese Patent Application No. 201990000012.0, filed on Mar. 12, 2019, Chinese Patent Application No. 201920199320.2, filed on Feb. 14, 2019, and Chinese Patent Application No. 201920198165.2, filed on Feb. 14, 2019. The contents of the above-mentioned patent applications are herein incorporated by reference.

TECHNICAL FIELD

The present disclosure relates to the technical field of personal care, and more particularly to a care instrument.

BACKGROUND

With the development of products in the field of personal care, people concern more and more about face and body care, from the outside appearance to internal health. Therefore, a variety of related massage instruments have appeared on the market, but most of these massage instruments have single massage function that is irrelevant to skin care products, and the materials used are relatively limited generally to either plastics or metal plating, resulting in certain limitations on the pH value of the care products. Therefore, these massage instruments do not really help the user to form a natural, healthy, or scientific care habit. Thus, it is necessary to develop personal care instruments with improved technologies and healthier materials in the field of personal care instruments to enhance their market competitiveness and help users achieve a truly healthy scientific skin care method.

In some embodiments, the present disclosure relates to a care instrument, which aims at solving the above technical problems in the prior art.

In some embodiments, in order to achieve the above objects, the following technical solutions are adopted by the present disclosure: a care instrument that includes a housing; a massaging component, a peristaltic pump, a control component, first and second conduits (e.g., pipes or tubes), and a power supply component, each of which is arranged within the housing; wherein the peristaltic pump is configured to connect with a storage container via the first conduit, the storage container being configured for accommodating a care product (e.g., an essential oil); the power supply component is configured to be in electrical connection with the massage component, the peristaltic pump, and the control component, respectively; the housing defines therein a liquid outlet penetrating the housing, and the peristaltic pump is in communication with the liquid outlet via a second conduit.

In some embodiments, the storage container comprises a first storage outlet; the peristaltic pump defines therein a liquid through hole; the first conduit has first and second ends, the first end of the first conduit is in communication with the first storage outlet, and the second end of the first conduit is in communication with the liquid through hole. In some embodiments, an adapting piece is fixedly arranged at one end of the first conduit, and the storage container is configured to detachably connect with the adapting piece.

In some embodiments, the storage container further comprises a second storage outlet, and the second storage outlet is in connection with a third conduit configured to balance the air pressure within the storage container.

In some embodiments, the third conduit is connected with a first pressure balancing component.

In some embodiments, the peristaltic pump has an air inlet and an air outlet in communication with each other, the third conduit has first and second ends, the first end of the third conduit is in communication with the second storage outlet, and the second end of the third conduit is in communication with the peristaltic pump through the air outlet of the peristaltic pump.

In some embodiments, the air inlet of the peristaltic pump is in communication with a fourth conduit configured to balance the air pressure within the storage container.

In some embodiments, the fourth conduit is connected with a second pressure balancing component.

In some embodiments, the housing comprises multiple liquid outlets; the second conduit comprises a main conduit and multiple branch conduits communicating with the main conduit; the main conduit is in connection with the peristaltic pump; and an end part of each branch conduit is in communication with a corresponding liquid outlet.

In some embodiments, the multiple liquid outlets are uniformly distributed with equal intervals, and the multiple branch conduits are in communication with the multiple liquid outlets.

In some embodiments, the storage container comprises a storage body and a storage lid, the first end of the first conduit is in connection with the storage lid, and the second storage outlet is located on the storage lid; and the storage body and the storage lid are enclosed to form the storage container.

In some embodiments, the storage lid is provided with a pipette having first and second ends, and the pipette is in communication with the first conduit.

In some embodiments, the first end of the pipette is in communication with the first conduit, and the second end of the pipette is provided with a gravity ball communicating with the pipette.

In some embodiments, an inner wall of the storage container forms an arc structure.

In some embodiments, the housing further comprises a temperature control component configured to control a surface temperature of the housing, and the temperature control component is in electrical connection with the control component and the power supply component, respectively.

In some embodiments, the housing comprises a material selected from the group consisting of jade (e.g., green jade and white jade), quartz (e.g., rose quartz, amethyst, and green aventurine), tetrahertz ore, basalt, or a combination thereof.

In some embodiments, the massage component is a vibrator.

In some embodiments, the massage component can be a component configured to provide illumination, weak current stimulation, temperature control adjustment, radio frequency, vibration, or other forms of care or massage on the user.

In some embodiments, the control component is a Printed Circuit Board Assembly (PCBA).

In some embodiments, the control component can adjust the pumping speed of the peristaltic pump by controlling either the current or the voltage of the peristaltic pump.

In some embodiments, the control component can adjust the vibration of the massage component by controlling either the current or the voltage of the massage component.

In some embodiments, the temperature control component can be a Peltier component or a thermoelectric cooler (TEC).

In some embodiments, the temperature control component can also include a temperature sensor such that the temperature of a part of the housing can be adjusted by the temperature control component based on the input from the temperature sensor.

Compared with the prior art, by including a massage component, a control component, and a power supply component that supplies power to the massage component, and the control component, the care instrument of the present disclosure can control the massage component through the control component, so as to allow a user to massage the user's face or body by using the care instrument. Further, by configuring one or more storage containers and the peristaltic pumps, and by including in each of the storage container a care product (e.g., an essential oil) which can be used to provide care (e.g., to moisturize skin or to treat skin conditions) and aroma to the user, each of the peristaltic pumps can transfer the care product from the corresponding storage container to one or more outlets at the surface of the housing, and discharge it to the environment through the one or more outlets. In other words, during use, the care instrument can provide both a massage function and provide an aroma therapy to a user simultaneously. In addition, the control component can control the drive components to deliver the care product to the surface of the housing in a timed and quantitative manner, so as to realize a precise delivery of the care product. In one embodiment, the control component can control the pumping speed of the peristaltic pumps via a pre-set program. In addition, when the massage component is operated in synchronization with the peristaltic pumps that deliver the care product, the care product can be transported to the surface of the housing during massage and can be further uniformly dispersed by the care instrument for easier application to the face or the body, thereby effectively improving the user experience.

DESCRIPTION OF THE DRAWINGS

In order to more clearly illustrate the technical solutions in the embodiments of the present disclosure, the drawings used in the description of the embodiments will be briefly described below. The following drawings illustrate only some embodiments of the present disclosure.

In the drawings, reference numerals are as follows:

10. Housing; 11. Through hole; 15. Locking groove; 20. Massaging component; 30. Peristaltic pump; 31. Second conduit; 32: Liquid through hole; 311. Main conduit; 312. Branched conduit; 40. Storage container; 41. First conduit; 42. First storage outlet; 47. Second storage outlet; 411. Adapting piece; 43. Third conduit; 431. First pressure balancing component; 44. Fourth conduit; 441. Second pressure balancing component; 45. Container lid; 46. Container body; 451. Pipette; 452. Gravity ball; and 50. Control component.

DETAILED DESCRIPTION

Embodiments of the present disclosure are described in detail below, and the examples of the embodiments are illustrated in the drawings, in which, the same or similar reference numerals are used to refer to the same or similar elements or elements having the same or similar functions. The embodiments described below with reference to the accompanying FIGS. 1-6 are intended to explain the application rather than to limit the present disclosure.

It should be understood that terms "length", "width", "upper", "lower", "front", "rear", "left", "right", "vertical", "horizontal", "top", "bottom", "inside", "outside" and the like indicating orientation or positional relationship are based on the orientation or the positional relationship shown in the drawings, and are merely for facilitating and simplifying the description of the present disclosure, rather than indicating or implying that a device or component must have a particular orientation, or be configured or operated in a particular orientation, and thus should not be construed as limiting the application.

Moreover, the terms "first" and "second" are adopted for descriptive purposes only and are not to be construed as indicating or implying a relative importance or indicating the number of technical features indicated. Thus, features prefixed by "first" and "second" will explicitly or implicitly represent that one or more of the referred technical features are included. In the description of the present disclosure, the meaning of "a plurality of" or "multiple" is two or more unless otherwise specifically defined.

In the present disclosure, unless otherwise specifically stipulated and defined, terms like "install", "connect", "couple", "fix" should be construed broadly, for example, they may indicate a fixed connection, a detachable connection, or an integral as a whole; may be a mechanical connection, or an electrical connection; may be in direct connection, or indirect connection via an intermediate, and may also reflect internal connection of two elements or interactions between two elements. For those skilled in the art, the specific meanings of the above terms in the present disclosure can be understood according to specific situations.

Figure 1:
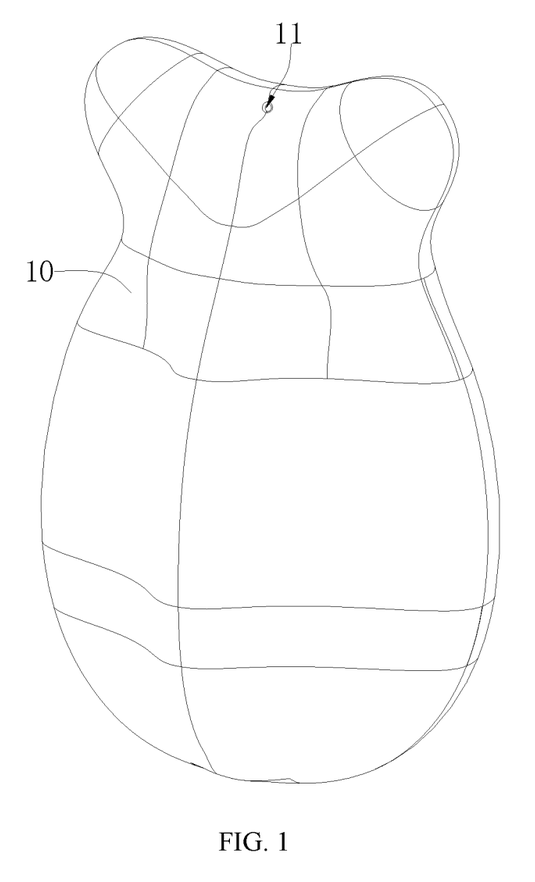
FIG. 1 is a first structural schematic view of a care instrument provided by one embodiment of the present disclosure.
Figure 2:
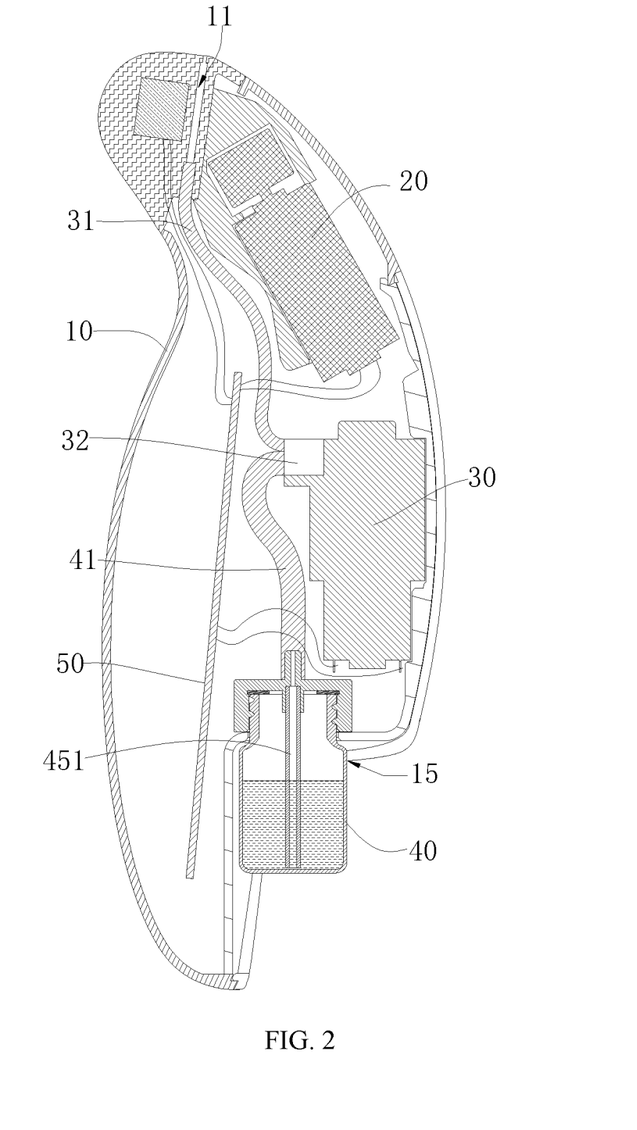
FIG. 2 is a cross-sectional schematic view of a care instrument provided by one embodiment of the present disclosure.

As shown in FIGS. 1-2, one embodiment of the present disclosure provides a care instrument comprising: a housing 10, a massaging component 20, a peristaltic pump 30, a control component 50, and a power supply component (not shown in FIGS. 1-6), all of which are arranged within the housing 10. The power supply component is configured to be in electrical connection with the massage component 20, the peristaltic pump 30, and the control component 50, respectively.

In some embodiments, the housing 10 comprises a material selected from the group consisting of jade (e.g., green jade and white jade), quartz (e.g., rose quartz, amethyst, and green aventurine), tetrahertz ore, basalt, or a combination thereof.

In some embodiments, the power supply device is a power source arranged inside the housing 10, or a conductive device configured to be electrically connected with an external power source.

In some embodiments, the massage component 20 is a vibrator. It can provide vibration at specified frequencies, such as from 75-200 Hz. The massage component 20 can allow the entire care instrument to vibrate. When the vibrating care instrument is applied to a user, it can help the user relax, increase blood circulation, and facilitate the application of the care product. In some embodiments, the massage component 20 can be a device configured to provide illumination, weak current stimulation, temperature adjustment, radio frequency, vibration, or other forms of care or massage on the user.

In some embodiments, the control component 50 is a Printed Circuit Board Assembly (PCBA). In some embodiments, the control component 50 can adjust the pumping speed of the peristaltic pump 30 by controlling either the current or the voltage of the peristaltic pump 30. In some embodiments, the control component 50 can adjust the vibration of the massage component 20 by controlling either the current or the voltage of the massage component 20.

As shown in FIGS. 1-2, in some embodiments, the peristaltic pump 30 is in connection with a storage container 40 configured for accommodating a care product (e.g., an essential oil, a moisturizer, a medicine, a topical ointment, a cream, a perfume, a massage oil, a cosmetic product, etc.).

The storage container 40 is in connection with the peristaltic pump 30 via a first conduit 41. The peristaltic pump 30 is in connection with the second conduit 31, the housing 10 defines therein one or more liquid outlets 11 penetrating the housing 10, and the second conduit 31 is in communication with the liquid outlets 11. The storage container 40 contains the care product.

Specifically, the storage container 40 may be arranged at least partially within the housing 10, and may also be arranged outside the housing 10. It is only required to store the care product in the storage container 40, so that peristaltic pump 30 can draw the care product out.

In some embodiments, the housing 10 is further provided with one or more catching grooves, each catching groove corresponds to the position of each of the one or more storage containers, and the one or more storage containers are configured to be attached to or removed from the housing through the catching grooves.

In some embodiments, the housing further comprises a temperature control component configured to control a surface temperature of the housing, and the temperature control component is in electrical connection with the control component 50 and the power supply component, respectively. The temperature control component can be a Peltier device or a thermoelectric cooler (TEC). In some embodiments, the temperature control component can also include a temperature sensor such that the temperature of a part of the housing can be adjusted by the temperature control component based on the input from the temperature sensor.

In some embodiments, in the care instrument provided, the control component 50 can be configured to control the massaging component 20, such that the care instrument can be used to massage the face or body of the user and thereby achieve the massage function. By further including the storage container 40 and the peristaltic pump 30, with the storage container 40 accommodating the care product that can be used to provide care (e.g., to moisturize the skin) for the user or add fragrance or aroma to the user, the peristaltic pump 30 can be configured to draw the care product from the storage container 40 and deliver the care product to a surface of the housing 10. In this way, the user can synchronously apply the care product for user care while using the care instrument to massage a portion of the body. The massaging component 20 and the peristaltic pump 30 can operate independently. In addition, by controlling the peristaltic pump 30 using the control component 50, the user can deliver the care product to the surface of the housing in a timed and quantitative manner, thereby achieving precise and accurate delivery of the care product. For example, the control component 50 may control the speed of peristaltic pump 30 by controlling the electric current and voltage of the peristaltic pump 30 via a pre-set program. When the massaging component 20 operates independently, the care instrument can provide massage functions; when the peristaltic pump 30 operates independently, the care product accommodated in the storage container 40 can be delivered to the surface of the housing, which enables the user to apply the care product onto his/her face or body. Moreover, when the massaging component 20 and the peristaltic pump 30 synchronously operate as a combination, the care product delivered to the surface of the housing may be further uniformly dispersed through the massage motion by the care instrument for better application of the care product onto the face or the body, and therefore effectively improves the user experience.

In some embodiments, the care product is a skin care product, an essential oil, or a perfume, or any liquid or gel-like care products that can be replaced according to the user's different needs. The specific types of the care products are not particularly limited.

In some embodiments, the massage component 20 can be a component configured to perform illumination, weak current stimulation, temperature control adjustment, radio frequency, vibration, or other forms of care or massage on the user.

Figure 3:
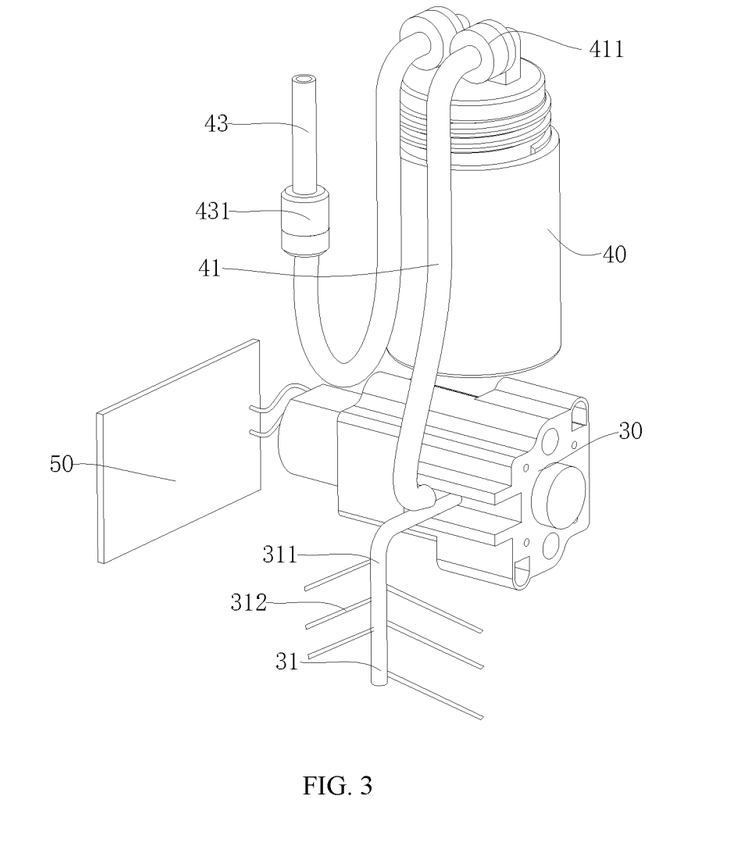
FIG. 3 is a first structural schematic view of a peristaltic pump and a storage container of a care instrument communicating with each other provided by one embodiment of the present disclosure.
Figure 5:
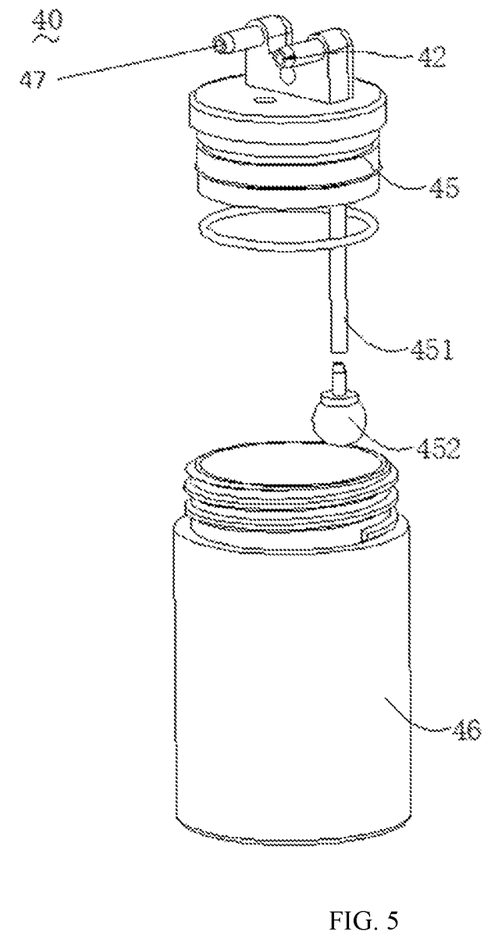
FIG. 5 is an exploded schematic view of a storage container provided by one embodiment of the present disclosure.
Figure 6:
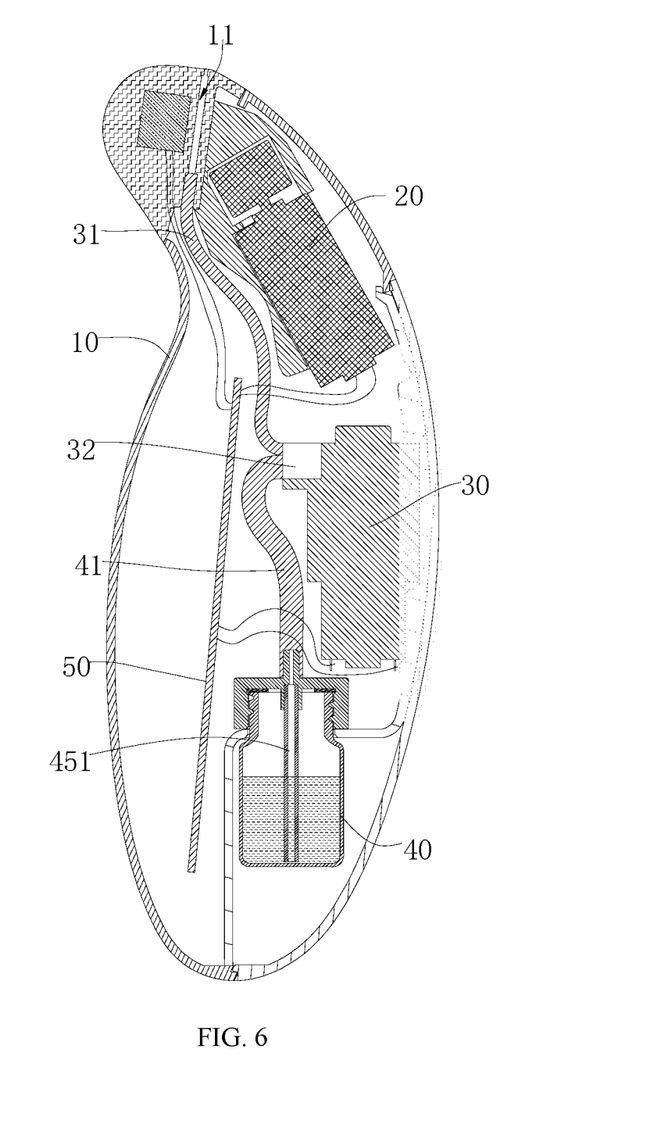
FIG. 6 is a second structural schematic view of a care instrument provided by one embodiment of the present disclosure.

In some embodiments, as shown in FIGS. 2, 3 and 5, the first conduit 41 has a first end and a second end. The storage container 40 defines therein a first storage outlet 42. The peristaltic pump 30 defines therein a liquid through hole 32, the first end of the first conduit 41 is in communication with the first storage outlet 42, and the second end of the first conduit 41 is in communication with the liquid through hole 32. By including the first storage container 40 having the first storage outlet 42 in the storage container 40, care product can be delivered to the surface of the housing 10 through the first conduit 41 for its use by the user.

In some embodiments, the housing 10 further defines therein with a locking groove 15 which corresponds to a position of the storage container 40, and the storage container 40 can be detachably installed in the locking groove 15 or detached from the locking groove 15. When the care product within the storage container 40 has been used up or needs to be replaced, the care product can be replenished into the storage container 40 after the storage container 40 is detached from the housing 10.

In some embodiments, when the care instrument is used by the user to provide massage functions, the user can operate the care instrument by operating the control component 50, the peristaltic pump 30 is instructed to start to operate by the control component 50, the care product within the storage container 40 is delivered to the surface of the housing 10 by the peristaltic pump 30, thereby achieving the synchronous massaging and delivery of care product for the user.

In one embodiment, the user can operate control component 50 through a first button and a second button on the housing 10. The first button changes the operation mode of the care instrument and the second button instructs the care instrument to start operating.

In some embodiments, as shown in FIGS. 3 and 5, an adapting piece 411 is fixedly arranged at one end of the first conduit 41, and the storage container 40 is in detachable connection with the adapting piece 411. Specifically, the first storage outlet 42 defines therein first internal threads, one end of the first conduit 41 is provided with the adapting piece 411, and an outer side of the adapting piece 411 defines thereon first external threads corresponding to the first internal threads, and the connection between first internal threads and the first external threads of the adapting piece 411 enable the communication between the first storage outlet 42 and the first conduit 41. Because the care product often has a certain degree of deposition due to precipitation or other reasons in use, which may result in clogging of the first conduit 41, by adopting the detachable connection between the first conduit 41 and the first storage outlet 42 through the adapting piece 411, the first conduit 41 can be replaced in case of the clogging of the first conduit 41, which enables the care instrument to be quickly restored.

In some embodiments, as shown in FIGS. 3 and 5, the storage container 40 further defines therein a second storage outlet (not shown), and the second storage outlet is in connection with a third conduit 43 configured to balance an air pressure within the storage container 40. Through the second storage outlet, the storage container 40 is in communication with the ambient environment, such that the air pressure within the storage container 40 is balanced, and further, when the care product is pumped out by the peristaltic pump 30, the storage container 40 can continuously supply the care product, thereby enabling the care instrument to work normally.

In some embodiments, as shown in FIG. 3, the third conduit 43 is provided thereon with a first pressure balancing component 431, and the first pressure balancing component 431 is in electrical connection with the power supply component and the control component 50. By including the first pressure balancing component 431 on the third conduit 43, on the one hand, when the care instrument is in normal operation, the peristaltic pump 30 draws the care product out of the storage container 40, while the first pressure balancing component 431 inflates the storage container 40 to balance the air pressure within the storage container 40; on the other hand, when the care instrument stops operation, in order to prevent the care product from corroding the first conduit 41 and the second conduit 31, the control component can control the peristaltic pump 30 to operate reversely, such that the care product within the first conduit 41 and the second conduit 31 can flow back to the storage container 40. In order to maintain the balance of the air pressure within the storage container 40, the air within the storage container 40 can be discharged out via the third conduit 43. However, because the standing angle of the care instrument after use is random, the care product may also be discharged out of the third conduit 43 at the same time the air is discharged through the third conduit 43. By arranging the first pressure balancing component 431, the care product will not flow out through the third conduit 43, which further prevents leakage of the liquid and the waste of the care product.

Figure 4:
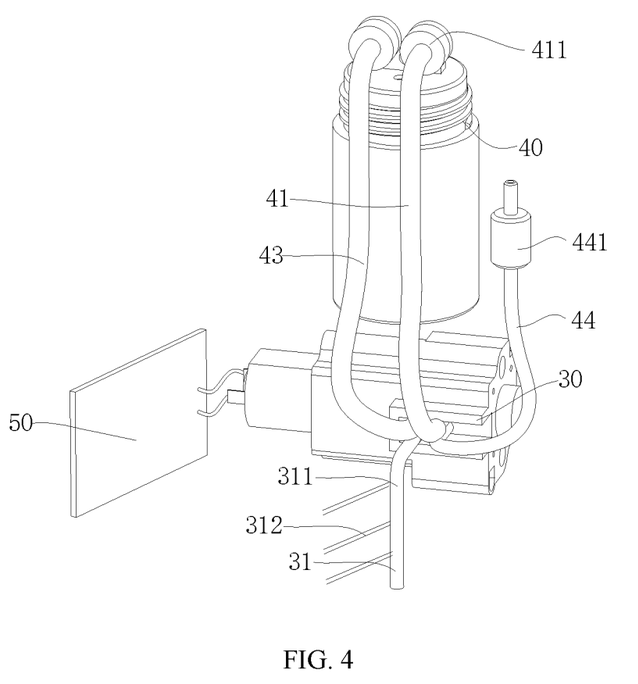
FIG. 4 is a second structural schematic view of a peristaltic pump and a storage container of a care instrument communicating with each other provided by one embodiment of the present disclosure.

In some embodiments, as shown in FIGS. 3-4, the second conduit 31 comprises a main pipeline 311 and multiple branched pipelines 312 communicating with the main pipeline 311; the main pipeline 311 is in fluid connection with the peristaltic pump 30, and an end part of each of the multiple branched pipelines 312 is in fluid communication with a corresponding liquid outlet 11. By including the multiple branched pipelines 312, the care product can be discharged onto the housing 10 through the multiple branched pipelines 312, such that the care product is uniformly applied onto the housing 10, thereby being effectively and conveniently used by the user.

In some embodiments, multiple liquid outlets 11 can be uniformly distributed (e.g., with equal intervals), and the multiple branched pipelines 312 can be in fluid communication with the multiple liquid outlets 11. By the uniform arrangement of the liquid outlets 11, the care product can be uniformly discharged onto the housing 10, further facilitating its application to a portion of the body by the user.

In some embodiments, as shown in FIGS. 2-5, the storage container 40 has a container body 46 and a container lid 45, one end of the first conduit 41 is in connection with the container lid 45, and the second storage outlet is defined in the container lid 45. The container body 46 is in detachable connection with the container lid 45. By configuring the container body 46 and the container lid 45 to be in detachable connection, the container body 46 can be detached from the container lid 45, which facilitates the addition of the care product to the storage container 40, thereby achieving long term use.

In some embodiments, as shown in FIGS. 2-5, the container lid 45 is provided with a pipette 451, and the pipette 451 is in communication with the first conduit 41. Since the position of the care instrument changes along with the hand of the user in use, the angle of the care instrument thereof varies. When the storage container 40 only contains a small amount of the care product, it is possible that the care product may be unable to be discharged onto the housing 10, with the arrangement of the pipette 451 in fluid communication with the first conduit 41, the pipette 451 being placed within the storage container 40, the care product can enter the first conduit 41 via the pipette 451, thereby ensuring the stability and continuity of the liquid discharging.

In some embodiments, as shown in FIG. 5, the pipette 451 has a first end and a second end. The first end of the pipette 451 is in fluid communication with the first conduit 41, and the second end of the pipette 451 is provided with a gravity ball 452 connected with the pipette 451. When the care instrument is rotated in use by the user, the care product is always located in the direction of gravity in the storage container 40, and accumulated in a bottom end of the storage container 40. By including the gravity ball 452, the gravity ball 452 is always at the bottom end of the storage container 40 when the angle of the care instrument changes. In other words, the gravity ball 452 is in real-time contact with the care product, so that all the care product in the storage container 40 can be discharged.

In some embodiments, an inner wall of the storage container 40 is in an arc structure. By arranging the inner wall of the storage container 40 to be in an arc structure, on the one hand, all the care product in the storage container 40 can be completely discharged with the help of the gravity ball 452, thereby avoiding waste of care product; on the other hand, this design avoids contamination from leftover care products when the care product is replenished, thereby effectively improving the user experience.

In some embodiments, as shown in FIG. 4, the third conduit 43 has a first end and a second end. The first end of the third conduit 43 is in fluid communication with the second storage outlet, and the second end of the third conduit 43 is in fluid communication with the peristaltic pump 30. By connecting the first end of the third conduit 43 to the second storage outlet, and connecting the second end thereof to the peristaltic pump 30, the air pressure within the storage container 40 can be balanced, and after the completion of the discharge of the care product, the storage container 40, the first conduit 41, the peristaltic pump 30, and the third conduit 43 together form an enclosed loop, allowing all the care product within the loop to flow back to the storage container 40.

In some embodiments, as shown in FIG. 4, the peristaltic pump 30 has an air inlet hole and an air outlet hole communicating with each other, and the air outlet hole is in fluid communication with the second end of the third conduit 43. By including the air inlet hole and the air outlet hole and connecting the air outlet hole with the third conduit 43, the air outlet hole is in fluid communication with the storage container 40, which further balances the air pressure within the storage container 40.

In some embodiments, the control component 50 is capable of controlling the peristaltic pump 30 to operate reversely, which enables the care product within the first conduit 41 and the second conduit 31 to flow back to the storage container 40. In such embodiments, the air inlet hole allows discharging air, and the air is drawn in through the air outlet hole so as to ensure the balance of the air pressure within the storage container 40.

In some embodiments, as shown in FIG. 4, the air inlet hole is in fluid communication with a fourth conduit 44 configured to balance the air pressure within the storage container 40. In this way, the care product discharged onto the housing 10 through the second conduit 31 will not return to the storage container 40 due to siphon effect. The care product discharged onto the housing 10 will likely be contaminated by touching the user's skin. This design prevents the contaminated care product from returning to the storage container 40 and prevents contamination of the care product in the storage container 40, ensuring the normal functioning of the care instrument.

In some embodiments, as shown in FIG. 4, the fourth conduit 44 is provided thereon with a second pressure balancing component 441, and the second pressure balancing component 441 is in electrical connection with the power supply component and the control component 50. In one embodiment, the second pressure balancing component 441 can be an air pump or a one-way check valve. In this way, on the one hand, when the care instrument is in normal operation, the peristaltic pump 30 draws the care product out of the storage container 40, while the second pressure balancing component 441 provides air to the storage container 40 to balance the air pressure within the storage container 40; on the other hand, when the care instrument stops operation, in order to prevent the care product from corroding the first conduit 41 and the second conduit 31, the control component can control the peristaltic pump 30 to operate reversely, such that the care product within the first conduit 41 and the second conduit 31 can flow back to the storage container 40. The storage container 40, the first conduit 41, the peristaltic pump 30, the fourth conduit 44, and the third conduit 43 together form an enclosed loop. In order to maintain the balance of the air pressure within the storage container 40 in the reverse operation mode, the air within the storage container 40 is discharged via the fourth conduit 44. However, because the standing angle of the care instrument may vary, the care product may also be discharged via the fourth conduit 44. The second pressure balancing component 441 prevents the care product from flowing out through the fourth conduit 44, preventing leakage and the waste of the care product.

In some embodiments, the first conduit 41, second conduit 31, the main conduit 311, branch conduits 312, the third conduit 43 or the fourth conduit 44 has an outer diameter of 3-5 millimeters and an inner diameter of 0.5-2 millimeter.

In some embodiments, the first conduit 41, second conduit 31, the main conduit 311, branch conduits 312, the third conduit 43 or the fourth conduit 44 has a hardness of 30 A-50 A as measured by an ASTM D2240 Type A Shore durometer.

The above is only the preferred embodiments of the present disclosure, and is not intended to limit the application. Any modifications, equivalent substitutions, and improvements made within the spirit and principles of the present disclosure are included in the protection scope of the present disclosure.

What is claimed is:

1. A care instrument, comprising:
a housing;
a massaging component, a temperature control component, a control component, and a power supply component, each of which is arranged within the housing;
wherein:
the power supply component is configured to be in electrical connection with the massaging component, the temperature control component, and the control component, respectively;
the temperature control component is configured to control a surface temperature at a surface of the housing comprising jade, quartz, amethyst, green aventurine, tetrahertz ore, basalt, or combinations thereof.

2. The care instrument of claim 1, further comprising a peristaltic pump, a first conduit, and a storage container, wherein the storage container comprises a first storage outlet; the peristaltic pump defines therein a liquid through hole; the first conduit has first and second ends, a first end of the first conduit is in communication with the first storage outlet, and a second end of the first conduit is in communication with the liquid through hole.

3. The care instrument of claim 2, wherein an adapting piece is fixedly arranged at one end of the first conduit, and the storage container is configured to detachably connect with the adapting piece.

4. The care instrument of claim 2, wherein the storage container further comprises a second storage outlet, and the second storage outlet is in connection with a third conduit configured to balance the air pressure within the storage container.

5. The care instrument of claim 4, wherein the storage container comprises a storage body and a storage lid, the first end of the first conduit is in connection with the storage lid, and the second storage outlet is located on the storage lid; and the storage body and the storage lid are enclosed to form the storage container.

6. The care instrument of claim 5, wherein the storage lid is provided with a pipette having first and second ends, and the pipette is in communication with the first conduit.

7. The care instrument of claim 6, wherein the first end of the pipette is in communication with the first conduit, and the second end of the pipette is provided with a gravity ball communicating with the pipette.

8. The care instrument of claim 7, wherein an inner wall of the storage container forms an arc structure.

9. The care instrument of claim 4, wherein the third conduit is connected with a first pressure balancing component.

10. The care instrument of claim 4, wherein the peristaltic pump has an air inlet and an air outlet in communication with each other, the third conduit has first and second ends, the first end of the third conduit is in communication with the second storage outlet, and the second end of the third conduit is in communication with the peristaltic pump through the air outlet of the peristaltic pump.

11. The care instrument of claim 10, wherein the air inlet of the peristaltic pump is in communication with a fourth conduit configured to balance the air pressure within the storage container.

12. The care instrument of claim 11, wherein the fourth conduit is connected with a second pressure balancing component.

13. The care instrument of claim 1, wherein:
the housing comprises multiple liquid outlets;
a second conduit connects the peristaltic pump to the multiple liquid outlets, the second conduit comprising a main conduit and multiple branch conduits communicating with the main conduit;
the main conduit is in connection with the peristaltic pump; and
an end part of each branch conduit is in communication with a corresponding liquid outlet.

14. The care instrument of claim 13, wherein the multiple liquid outlets are uniformly distributed with equal intervals.

15. The care instrument of claim 1, wherein the temperature control component is in electrical connection with the control component and the power supply component, respectively.

16. The care instrument of claim 1, wherein the temperature control component comprises a Peltier element or a thermoelectric cooler.

17. The care instrument of claim 1, further comprising a temperature sensor to provide a temperature of a part of the housing to the control component.

18. The care instrument of claim 1, wherein the housing has a pH value different from plastic and metal.

19. A care instrument, comprising:
a housing including a material comprising jade, quartz, amethyst, green aventurine, tetrahertz ore, basalt, or combinations thereof;
a massaging component, a temperature control component, a control component, and a power supply component, each of which is arranged within the housing;
wherein the power supply component is configured to be in electrical connection with the massaging component, the temperature control component, and the control component, respectively; and
wherein the temperature control component is configured to control a surface temperature at a surface of the housing.

20. A care instrument, comprising:
a housing;
a massaging component, a peristaltic pump, a control component, a first conduit, a second conduit, a third conduit, and a power supply component, each of which is arranged within the housing;
a storage container comprising a first storage outlet and a second storage outlet, the second storage outlet in connection with the third conduit and configured to balance air pressure within the storage container;
wherein
the peristaltic pump defines a liquid through hole;
the first conduit has a first end and a second end, the first end in communication with the first storage outlet, the second end in communication with the liquid through hole;
the peristaltic pump is configured to connect with the storage container via the first conduit, the storage container being configured for accommodating a care product;
the power supply component is configured to be in electrical connection with the massaging component, the peristaltic pump, and the control component, respectively; the housing defines therein a liquid outlet penetrating the housing, and the peristaltic pump is in communication with the liquid outlet via a second conduit; and
the peristaltic pump has an air inlet and an air outlet in communication with each other, the third conduit has a first conduit end and a second conduit end, the first conduit end is in communication with the second storage outlet, and the second conduit end is in communication with the peristaltic pump through the air outlet.

* * * * *